(12) United States Patent
Vanhelmont et al.

(10) Patent No.: US 12,158,440 B2
(45) Date of Patent: Dec. 3, 2024

(54) SENSOR DEVICE AND METHOD FOR OPERATING A SENSOR DEVICE

(71) Applicant: Sciosense B.V., AE Eindhoven (NL)

(72) Inventors: Frederik Willem Maurits Vanhelmont, Maaseik (BE); Nebojsa Nenadovic, Wijchen (NL); Hilco Suy, Son en Breugel (NL); Agata Sakic, Eindhoven (NL); Micha in't Zandt, Veldhoven (NL); Guido Stefanuto, Eindhoven (NL)

(73) Assignee: Sciosense B.V., AE Eindhoven (NL)

( * ) Notice: Subject to any disclaimer, the term of this patent is extended or adjusted under 35 U.S.C. 154(b) by 420 days.

(21) Appl. No.: 17/433,856

(22) PCT Filed: Feb. 26, 2020

(86) PCT No.: PCT/EP2020/055020
§ 371 (c)(1),
(2) Date: Aug. 25, 2021

(87) PCT Pub. No.: WO2020/178096
PCT Pub. Date: Sep. 10, 2020

(65) Prior Publication Data
US 2022/0128502 A1    Apr. 28, 2022

(30) Foreign Application Priority Data

Mar. 6, 2019  (EP) .................................... 19161056

(51) Int. Cl.
*G01N 27/12*    (2006.01)
*G01N 33/00*    (2006.01)

(52) U.S. Cl.
CPC ....... *G01N 27/123* (2013.01); *G01N 33/0031* (2013.01)

(58) Field of Classification Search
CPC .. G01N 27/123; G01N 27/124; G01N 33/007; G01N 33/0027; G01N 33/0031; G01D 3/036
See application file for complete search history.

(56) References Cited

U.S. PATENT DOCUMENTS 5,898,101 A    4/1999  Lyle et al.
7,692,148 B2   4/2010  Lane et al.
(Continued)

FOREIGN PATENT DOCUMENTS

CN    101563592 A    10/2009
CN    105043439 A    11/2015
(Continued)

OTHER PUBLICATIONS

Sensiron, the Sensor Company, "Datasheet SHT1x (SHT10, SHT11, SHT15) Humidity and Temperature Sensor IC, " www.sensirion.com, Version 5, Dec. 2011, 12 pages.
(Continued)

*Primary Examiner* — Benjamin R Schmitt
(74) *Attorney, Agent, or Firm* — Slater Matsil, LLP

(57) ABSTRACT

A sensor device includes a first sensor including a heating element configured to heat up the first sensor in a controllable manner and a second sensor thermally coupled to the heating element of the first sensor such that the heating element is further configured to heat up the second sensor in a controllable manner.

13 Claims, 3 Drawing Sheets

(56) References Cited

U.S. PATENT DOCUMENTS

| | | | |
|---|---|---|---|
| 9,417,309 B1* | 8/2016 | Fan | G01R 35/005 |
| 2012/0253691 A1 | 10/2012 | Graf et al. | |
| 2013/0295697 A1* | 11/2013 | Hanan | G01R 31/2884 |
| | | | 257/E21.53 |
| 2014/0374848 A1* | 12/2014 | Koh | H01L 23/315 |
| | | | 257/415 |
| 2016/0169704 A1 | 6/2016 | Badeja et al. | |
| 2018/0136762 A1 | 5/2018 | Jeong et al. | |

FOREIGN PATENT DOCUMENTS

| | | | | |
|---|---|---|---|---|
| CN | 105339764 A | 2/2016 | | |
| CN | 205342406 U | 6/2016 | | |
| CN | 206590895 U | 10/2017 | | |
| CN | 108074486 A | 5/2018 | | |
| DE | 19642107 A1 | 4/1998 | | |
| DE | 102005042485 A1 | 3/2007 | | |
| WO | WO-2013060441 A2 * | 5/2013 | | G01D 3/036 |

OTHER PUBLICATIONS

Silicon Labs, "Si70xx Humidity and Temperature Sensor Designer's Guide," Silicon Laboratories, Rev. 1.7, AN607, 2015, 41 pages.

* cited by examiner

SENSOR DEVICE AND METHOD FOR OPERATING A SENSOR DEVICE

This patent application is a national phase filing under section 371 of PCT/EP2020/055020, filed Feb. 26, 2020, which claims the priority of European patent application 19161056.7, filed Mar. 6, 2019, each of which is incorporated herein by reference in its entirety.

TECHNICAL FIELD

The present disclosure relates to a sensor device comprising a first sensor and a second sensor, and to a method for operating said sensor device.

BACKGROUND

Various applications employ a plurality of sensors for being able to sense a multitude of different quantities. Alternatively, or in addition, further sensors may be employed for correcting measurement results of a main sensor that is cross-sensitive to multiple quantities. Common examples for this are environmental sensors such as gas sensors, whose behavior may also be dependent on humidity. As many applications have strict size requirements due to a confined volume, multiple sensors are advantageously provided on a single sensor device. However, different sensor types may each require specific operating conditions such as temperature, for instance. Present day sensor devices with multiple sensors therefore employ sensors that are each provided with their dedicated means of establishing the required operating conditions. This may, however, lead to complicated designs of such sensor devices having plentiful components.

SUMMARY

Embodiments to provide an improved concept of a sensor device having multiple sensors and of a method of operating such a sensor device.

In embodiments, the improved concept is based on the idea of combining a first sensor and a second sensor in a sensor device, wherein the first sensor requires an operating temperature that is significantly above typical ambient temperatures of the sensor device. Furthermore, the improved concept suggests thermally coupling the second sensor to the means that establish the operating temperature of the first sensor, such that a temperature of the second sensor may be elevated above the ambient temperature according to its mode of operation without the necessity of providing a dedicated heater to the second sensor.

For example, a sensor device according to the improved concept comprises a first sensor and a second sensor, wherein the first sensor comprises a heating element that is configured to heat up the first sensor in a controllable manner. Furthermore, the second sensor is thermally coupled to the first sensor, e.g. to the heating element of the first sensor, such that the heating element is further configured to heat up the second sensor in a controllable manner.

The first sensor and the second sensor may have the same or a different operating temperature. For example, in a sensing mode of operation the first sensor is heated to a temperature that is significantly higher than an ambient temperature of the sensor device. The second sensor in a sensing mode of operation may be operated at an operating temperature that corresponds to, or is higher than, the ambient temperature. For different modes of operation, the second sensor may be heated to specific temperature set points that depend on the specific mode of operation.

The sensor device may comprise further sensors that are either thermally coupled to the first sensor, e.g. to the heating element, or they are thermally isolated.

Heating the sensors in a controllable manner means, for example, heating the first and the second sensor and potential further sensors by means of the heating element that is controlled by a control circuit, such as a servo loop. The sensor device may comprise the control circuit or control connections for connecting an external control circuit.

The sensor device may further comprise integrated circuitry, such as an application-specific integrated circuit, ASIC, for reading out sensor values from the sensors of the sensor device. Alternatively, the sensor device comprises readout connections for connecting an external readout circuit.

In some embodiments, the first sensor is a gas sensor, e.g. a metal oxide gas sensor, and the second sensor is an environmental sensor, such as a humidity sensor configured to measure relative humidity of a gas surrounding the sensor device.

Gas sensors like metal oxide, MOX, gas sensors are employed to detect the presence of gases and/or to identify gas compounds of a gas surrounding the sensor. For example, MOX sensors are employed for reliable air quality monitoring. MOX sensors are a common choice for many applications as they are characterized by cost-efficient mass production, high sensitivity in the ppm range and long lifespans. However, the efficient operation of MOX sensor requires operating temperatures in the range of 150° C. to 500° C. Furthermore, MOX sensors typically show a significant cross-sensitivity to certain environmental factors such as humidity. Therefore, a sensor device comprising a MOX sensor advantageously further comprises an environmental sensor such as a humidity sensor, in order to enable readjustment of the measurement of the gas sensor.

Although a measurement of the second sensor in the described case is desirable at the environmental conditions, i.e. at the ambient temperature, of the sensor device, thermally coupling the second sensor to the heating element of the first sensor enables heating up the second sensor in a controllable manner and hence allows for additional modes of operation of the second sensor. For example, a heatable environmental sensor enables processes such as an enhanced calibration, self-diagnosis, aging-prevention and reconditioning of the second sensor.

In some embodiments for a sensing mode of operation the first sensor is heated up to an operating temperature that is between 300° C. and 500° C. For instance, the heating up occurs within a time of less than 2 seconds.

A fast heating up of the first sensor is desirable in order to allow for fast measurements. Particularly in cases in which the operating temperature of the second sensor differs from that of the first sensor, fast heating is desirable in order to achieve quasi simultaneous measurements from both sensors.

In some embodiments, the heating element is configured to heat up the second sensor to a maximum set point that is above an ambient temperature of an environment of the sensor device.

For example, the maximum set point is several tens of degrees above the ambient temperature. This enables processes for the second sensor such as calibration over a large range of temperatures and relative humidity conditions, reconditioning through evaporation of contaminants, aging-prevention and self-diagnosis. In contrast, present day environmental sensors often employ monolithically integrated heating elements that allow for a temperature delta of merely up to 5-10° C. The above-mentioned processes in this case cannot be performed efficiently such that additional means of heating up such sensors are necessary if the above-mentioned processes are desired. Higher temperature increases of sensors with monolithically integrated heating elements can be reached with special PCB layout and thermal design in combination with very high currents through the heating elements. However, for this special circuitry is needed so that these high currents can be achieved.

In some embodiments, the heating element is configured to heat up the second sensor at a lower rate compared to the first sensor.

Particularly in cases in which the second sensor operates at a significantly different temperature than the first sensor, a lower heating rate for the second sensor, for example realized by means of an intentional imperfect thermal coupling of the second sensor to the heating element, may enable efficient operation of both sensors at the same time. For example, the first sensor is rapidly heated to its operation temperature far above the ambient temperature while the second sensor at the same time stays within or close to its specified operation conditions, which for instance are at or close to the ambient temperature.

In some embodiments, the sensor device further comprises a temperature sensor which is configured to measure a momentary temperature of the second sensor.

For some environmental sensors such as relative humidity sensors, a measurement of actual ambient conditions requires precise knowledge of the second sensor's operating conditions that include the temperature of the second sensor. To this end, a temperature sensor may be arranged in the sensor device close to the second sensor such that its temperature can be measured accurately. With this measurement in combination with the sensor reading, actual ambient conditions, such as relative humidity of a surrounding gas, may be precisely calculated and/or estimated. Moreover, in order to efficiently heat up the second sensor to a certain set point, knowledge about its momentary temperature is likewise essential. For example, the temperature sensor is part of a control circuit and hence enables reliable control over the temperature of the second sensor.

In some embodiments, the first sensor is arranged on a first die and the second sensor is arranged on a second die. Therein, the first die and the second die are arranged in a single sensor package.

The first sensor and the second sensor may be fabricated according to different fabrication methods. For example, one of the two sensors comprises MEMS structures while the other sensor is fabricated following a purely CMOS-compatible process. In this case, an efficient fabrication means separate fabrication on dedicated dies. Moreover, the two sensors are co-packaged, i.e. they are arranged in a single package, in order to provide a compact sensor device with multiple different sensors. One of the two dies may further comprise active circuitry for reading out sensor values from all sensors, for instance.

In some embodiments the first sensor is arranged beside the second sensor, wherein both sensors are arranged on a surface of a substrate body. Alternatively, the first sensor is arranged on a surface of a substrate body of the second sensor.

Depending on specific requirements of the application, the first and the second sensor may either be arranged in the vicinity of each other, for example next to each other, on a common substrate or they may be arranged on top of each other. In both cases, the second sensor may be thermally coupled to the heating element of the first sensor, which for example comprises heating pads or hotplates. For example, the thermal coupling is realized by means of a material with an appropriate heat conductivity connecting the heating element and the second sensor.

In some embodiments, during a regular mode of operation the heating element is operated in a duty cycle. Therein, within an active time of the duty cycle the first sensor is operated in a sensing mode and the second sensor is operated in an idle mode. The sensors are operated vice versa within a passive time of the duty cycle.

For example, the first sensor is heated up in order to perform a measurement. To this end, an active time of a duty cycle may establish the operating temperature of the first sensor via an active heating element. In contrast, the operating temperature of the second sensor may be at or close to the ambient temperature. Therefore, the second sensor is operated during a passive time of the duty cycle, i.e. when the heating element is inactive and the first sensor and the second sensor thermalize to the ambient temperature. For example, the sensor device comprises a heat sink configured to rapidly thermalize the second sensor to the ambient temperature.

The above-mentioned object is further solved by an electronic device comprising a sensor device according to one of the embodiments described above.

Possible applications of a sensor device with multiple environmental sensors, such as a humidity sensor, a temperature sensor and a gas sensor, include environmental sensing applications for measuring and monitoring ambient conditions. To this end, a sensor device according to one of the embodiments described above may be employed in portable or wearable devices as well as in automotive solutions, for example for measuring and monitoring ambient conditions.

The above-mentioned object is further achieved by a method for operating a sensor device comprising a first and a second sensor. For instance, the first sensor comprises a heating element and the second sensor is thermally coupled to the first sensor, e.g. to the heating element. The method comprises in a controllable manner heating up the second sensor to a set point using the heating element of the first sensor.

In some embodiments of the method, in a calibration mode of operation of the second sensor, the method further comprises heating up the sensor to a number of calibration set points, and at each of the number of calibration set points recording a temperature-dependent measurement value with the second sensor. The method further comprises recording each measurement value with the corresponding one of the number of calibration set points in a calibration table and/or determining from the measurement values and the calibration set points calibration coefficients.

Providing a heating element of the first sensor, for example that of a MOX gas sensor, enables heating up the second sensor, which may be an environmental sensor, by several tens of degrees above an ambient temperature of the sensor device. Compared to conventional environmental sensors that have a monolithically integrated dedicated heating element that provides a temperature delta of merely up to 5-10° C., the improved concept allows for a calibration of the second sensor over a broad temperature and relative humidity range without having to change the ambient conditions of the sensor device. This leads to an efficient and fast calibration, and hence to a high accuracy of the calibrated first sensor. The broad temperature range therein is particularly relevant for applications such as automotive applications.

For instance, the calibration mode of operation comprises, in a first stage, exposing the sensor device to well-controlled ambient conditions at a certain temperature and humidity. Consequently, the heating element is set to heat up the second sensor to various calibration set points, at which measurements, for example of relative humidity, are obtained. Via a conserved quantity, such as the absolute humidity or the dew point, the actual value at each calibration set point can be calculated and compared to the measurement values. Based on this comparison, a calibration table, such as a lookup table, can be generated and/or calibration coefficients of a temperature- and/or humidity-dependent formula are determined.

In some embodiments, in a self-diagnosis mode of operation of the second sensor, the method further comprises recording a first measurement value of a temperature-dependent quantity with the second sensor being at a first test set point, and recording a second measurement value of the temperature-dependent quantity with the second sensor being at a second test set point. The method further comprises comparing the first measurement value to the second measurement value via a conserved quantity and based on a result of the comparison determining whether an error condition of the second sensor exists.

In order to determine whether the sensor operates correctly, a self-test may be performed, in which a sensor value is taken at different test set points. For example, a humidity sensor may be heated to a first set point, at which a first measurement value of relative humidity is acquired. An evaluation circuit, which is either integrated in active circuitry of the sensor device or which is external, may then calculate from the first measurement value and the first test set point an expected value at a second test set point. For example, the calculation may include a conserved quantity such as absolute humidity or the dew point. The second sensor is then thermalized to a second test set point, at which a second measurement value of relative humidity is acquired. The evaluation circuit may further be configured to compare the expected value with the second measurement value and, based on a result of the comparison, to determine whether an error condition of the second sensor exists. For example, the evaluation circuit may generate and output an error flag indicating an error status of the second sensor.

In some embodiments, in an aging-prevention mode of operation of the second sensor, the method further comprises detecting whether the second sensor is in a regime outside its specification, in particular in terms of environment conditions, and based on a result of the detection heating the second sensor to a temperature set point that is higher than an ambient temperature of the sensor device.

Particularly relative humidity sensors may experience a significant drift over their lifetime. This drift is typically caused by extended exposure to high humidity which causes a degradation of the sensor. If such large humidity is detected the sensor device may be configured to automatically heat up the second sensor and to stabilize it at a temperature above the ambient temperature in order to achieve a reduced local relative humidity.

In some further embodiments, in the aging-prevention mode of the second sensor, the method further comprises recording an uncorrected measurement value at the temperature set point and calculating from the uncorrected measurement value and the temperature set point a corrected measurement value at the ambient temperature.

If the temperature of the second sensor is elevated above the ambient temperature for aging-prevention, the correct value of a temperature-dependent quantity can be calculated via a conserved quantity. For example, the second sensor is a humidity sensor and configured to measure the local relative humidity. If the sensor is stabilized to an elevated temperature and therefore measures a value below the actual value a corrected value, corresponding to or estimating the actual value, can be obtained via the temperature of the second sensor and a conserved quantity such as absolute humidity or the dew point, assuming that the ambient temperature stays constant.

In some embodiments, in a reconditioning mode of operation of the second sensor the method further comprises heating the second sensor to a reconditioning set point that depends on a boiling point of a contaminating compound, and maintaining the second sensor at the reconditioning set point for an extended period such that the contaminating compound evaporates from the second sensor.

Exposing the second sensor to contaminants such as volatile organic compounds for an extended period of time may lead to a degradation or an impairment of the sensor. Likewise, exposing the sensor to a regime outside its specifications may lead to a saturation of a sensitive material, for instance. Typically, in these cases the sensor can be reconditioned by evaporating such contaminants by means of heating up the sensor to a temperature that depends on a boiling temperature of the contaminant. For example, in order to evaporate water from the second sensor the heating element may be controlled to heat up the second sensor to a temperature around 100° C. Other compounds may have a different boiling temperature that is smaller or larger than 100° C.

Further embodiments of the method according to the improved concept become apparent to a person skilled in the art from the described embodiments of the sensor device.

BRIEF DESCRIPTION OF THE DRAWINGS

The following description of figures of exemplary embodiments may further illustrate and explain aspects of the improved concept. Components and parts of the sensor device with the same structure and the same effect, respectively, appear with equivalent reference symbols. Insofar as components and parts of the sensor device correspond to one another in terms of their function in different figures, the description thereof is not repeated for each of the following figures.

DETAILED DESCRIPTION OF ILLUSTRATIVE EMBODIMENTS

Figure 1:
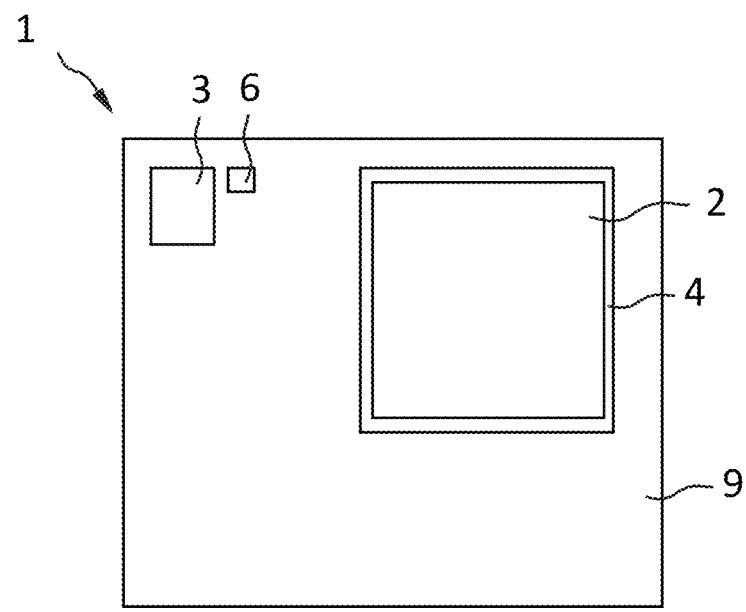
FIG. 1 shows a schematic top view of an exemplary embodiment of a sensor device according to the improved concept.

FIG. 1 shows a schematic top view of an exemplary embodiment of a sensor device 1 according to the improved concept. In this embodiment, the sensor device 1 comprises a substrate body 9 with a surface, on which the second sensor 3 and a temperature sensor 6 are arranged in close vicinity of each other. Close vicinity in this context means that a temperature measured at the location of the temperature sensor 6 corresponds to a temperature at the location of the second sensor.

The second sensor 3 is an environmental sensor such as a relative humidity sensor configured to measure a quantity of a gas 5 surrounding the sensor device 1. For example, the second sensor 3 is a capacitive humidity sensor comprising electrodes arranged as a capacitor and a sensitive material arranged between and/or around the electrodes. The temperature sensor 6 is for example a thermistor or a thermocouple or a PTAT circuit.

Furthermore, the heating element 4 and the first sensor 2 are arranged on the surface of the substrate body 9. For example, the heating element 4 is a hotplate such as a micro-hotplate and the first sensor 2 is arranged on the heating element 4. The second sensor 3 is for example a gas sensor such as a metal-oxide, MOX, gas sensor comprising one or more MEMS transducers. MOX gas sensors typically operate at 300° C. to 500° C. in a sensing mode of operation and therefore require a respective powerful heating element 4.

The substrate body 9 may also comprise an integrated circuit, which may be a CMOS circuit with active and/or passive circuitry such as an application-specific integrated circuit configured for reading out and evaluating values from the first sensor 2 and the second sensor 3. Such integrated circuits are known per se, and are not shown in the figures. The substrate body 9 may be a semiconductor substrate chip diced from a wafer, for instance. The surface of the substrate body 9 is, for example, a surface parallel to the main extension plane of the substrate body 9 and may be referred to as a top surface without loss of generality.

The substrate body 9 may be of a material with significant thermal conductivity such that the heating element 4 also increases the temperature of the second sensor 3. Alternatively, the substrate body may comprise heat conducting paths connecting the heating element 4 to the second sensor 3. The heat conductivity between the heating element 4 and the second sensor 3 may be dimensioned such that a maximum temperature increase of the second sensor 3 induced by the heating element 4 is in the order of several tens degrees Celsius.

The substrate body 9 may further comprise a control circuit for heating up the first sensor 2 and the second sensor 3 in a controllable manner. Alternatively, the substrate body 9 may comprise control connections for connecting an external control circuit. The control circuit may be a servo loop or a feedback control system and may use sensor readings from the temperature sensor 6 for controlling the temperature of the second sensor 3. The control circuit may further use sensor readings from a further temperature sensor that measures a temperature that corresponds to that of the first sensor 2.

The first sensor 2 and the heating element 4 may be arranged on a first die 7, such as a further substrate body, that is arranged on the substrate body 9. Alternatively or in addition, the second sensor 3 and the temperature sensor 6 may be arranged on a second die 8 that is arranged on the substrate body 9. Alternatively, the second die 8 can act as a substrate body for the first die 7.

Figure 2:
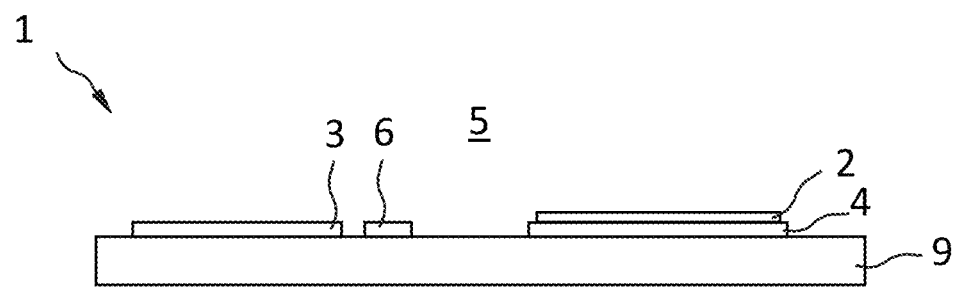
FIGS. 2, 3A, and 3B show schematic cross-sectional views of further exemplary embodiments of a sensor device.

FIG. 2 shows a cross-sectional view of the exemplary embodiment of the sensor device 1 shown in FIG. 1.

Figure 3A:
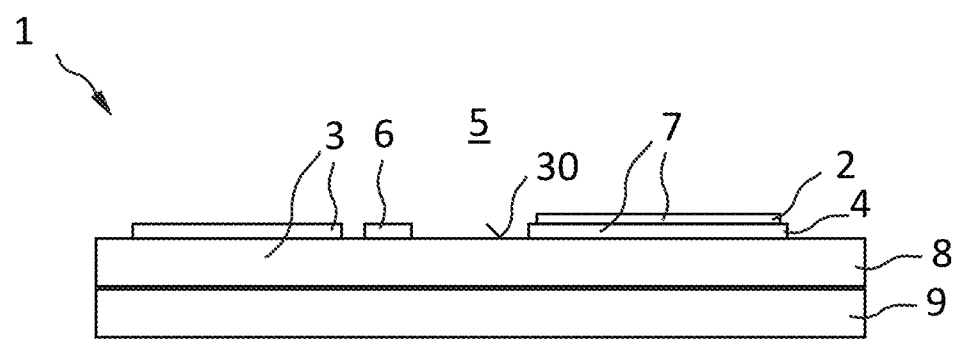

The exemplary embodiment according to FIG. 3A essentially corresponds to that of FIGS. 1 and 2. As shown in the cross-sectional view of FIG. 3A, the second die 8 may form a substrate body of the second sensor 3, wherein the first sensor 2 is arranged on a surface 30 of the substrate body, namely the second die 8. Thus, the first sensor 2 and the second sensor 3 are arranged on top of each other.

In this arrangement, the second sensor 3 is thermally coupled to the heating element 4 of the first sensor 2. The substrate body 9 underneath the second die 8 of the second sensor 3 may also be dispensed with.

Figure 3B:
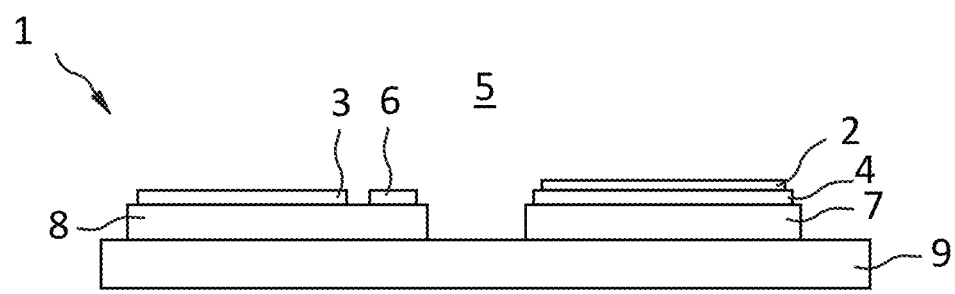

FIG. 3B shows a cross-sectional view of a further exemplary embodiment of the sensor device 1. In this embodiment, the heating element 4 and the first sensor 2 are arranged on a first die 7. The second sensor 3 together with the temperature sensor 6 are arranged on a second die 8. The first die 7 and the second die 8 are arranged on the surface of the substrate body 9. The second die 8 may comprise circuitry, such as a control circuit, to read out sensor values of the second sensor 3 and/or of the temperature sensor 6, for instance. Likewise, the first die 7 may comprise circuitry to control the heating element 4 and/or to read out sensor values of the first sensor 2.

In some cases, fabrication processes of the first sensor 2 and the second sensor 3 are not or only partially compatible with each other such that a separate fabrication is necessary. Also aspects like cost-effectiveness, yield, fabrication time and complexity of the overall process may be reasons for a separate fabrication process. For example, the first sensor 2 comprises MEMS structures such as MEMS transducers. Such MEMS structures may not be compatible with a purely CMOS compliant fabrication method of the second sensor 3, for instance.

The common substrate 9 enables the co-packaging of the first and the second sensors 2, 3 despite the separate dies. The substrate body 9 may act as a mediator for heat such that the second sensor 3 is heated by means of the heating element 4. Alternatively, heat conducting paths such as thermally conductive wire may be employed to thermally couple the heating element 4 and the second sensor 3.

Figure 4:
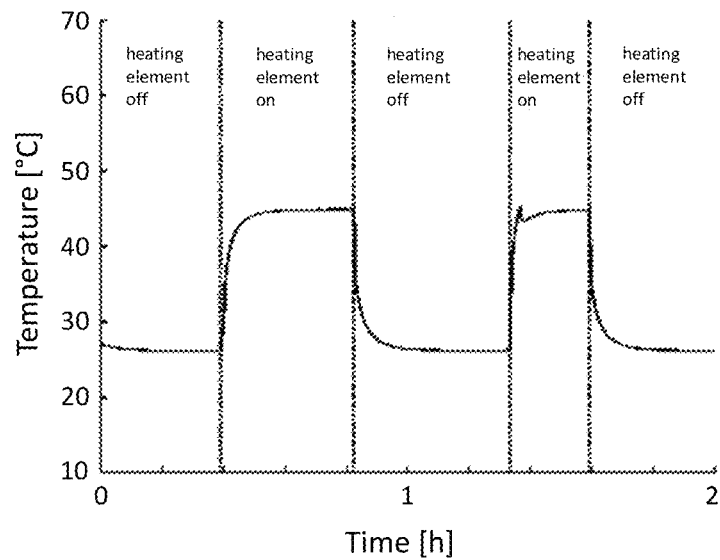
FIGS. 4 and 5 show exemplary data indicating the temperature behavior of the second sensor of an exemplary embodiment of a sensor device.
Figure 5:
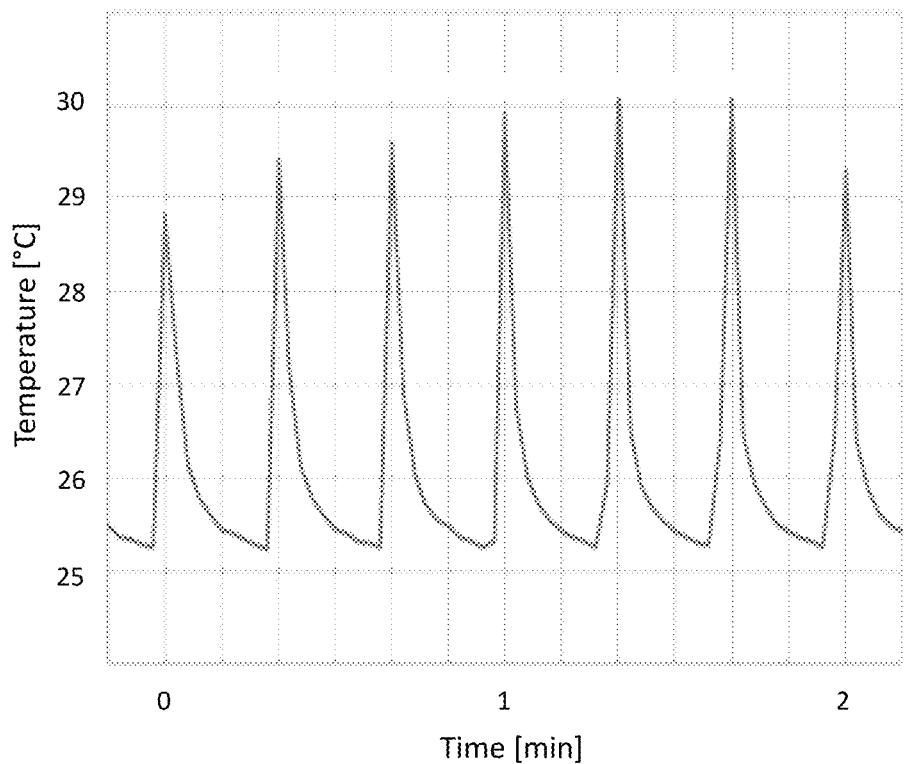

FIGS. 4 and 5 show exemplary data indicating the temperature behavior of the second sensor 3 of an exemplary embodiment of a sensor device 1.

FIG. 4 shows the temperature of the second sensor 3, for example measured via the temperature sensor 6 shown in the previous Figures, versus time. The sensor device 1 in this embodiment is engineered such that the heating element 4 of the first sensor 2 is capable of heating up the second sensor 3 and achieving a temperature of in this case 20° C. above the ambient temperature of the sensor device 1, which here is about 27° C. as can be seen from the minimum of the shown curve when the gas sensor, i.e. the heating element 4 of the first sensor 2, is switched off. By adjusting the distance between the two sensors 2, 3 and/or the thermal conductivity in between the two sensors 2, 3 the maximum temperature increase of the second sensor 3 may be adjusted according to requirements of the specific application.

A maximum temperature of the second sensor 3 that is several tens of degrees Celsius above the ambient temperature is desirable for different modes of operation of the second sensor 3, such as a calibration mode, a self-diagnosis mode, an aging-prevention mode and a reconditioning mode of operation.

FIG. 5 shows similar measurement data as shown in FIG. 4. In contrast to the previous measurement data, in this embodiment, the heating element 4 is operated in a duty cycle with a period of around 20 seconds and an active time of the heating element 4 of about 1.5 seconds within the duty cycle.

In this case, the maximum temperature increase of the second sensor 3 is merely in the order of 3° C. to 5° C. The aforementioned duty cycle represents a typical duty cycle of a MOX gas sensor, which is heated to its operating temperature within 1.5 seconds during a sensing mode of operation of the MOX sensor. As the temperature increase of the second sensor 3, whose operating temperature typically is at the ambient temperature of the sensor device 1, is relatively small accurate readings of the second sensor 3 can still be obtained. For example, the second sensor 3 operates in a sensing mode of operation during a passive time of the duty cycle, in which the second sensor 3 thermalizes close to the ambient temperature of in this case 25° C. During the active time, a self-diagnosis is still possible.

The embodiments shown in the FIGS. 1 to 5 as stated represent exemplary embodiments of the sensor device 1 and the temperature behavior of the second sensor 3. Therefore, they do not constitute a complete list of all embodiments according to the improved concept. Actual sensor device configurations may vary from the embodiments shown in terms of shape, size and materials, for example.

Although the invention has been illustrated and described in detail by means of the preferred embodiment examples, the present invention is not restricted by the disclosed examples and other variations may be derived by the skilled person without exceeding the scope of protection of the invention.

The invention claimed is:

1. A sensor device comprising:
a first die comprising a first sensor with a heating element configured to heat up the first sensor in a controllable manner; and
a second sensor thermally coupled to the first sensor such that the heating element is further configured to heat up the second sensor in a controllable manner,
wherein the second sensor comprises a substrate body, the substrate body being a second die comprising an integrated circuit and the second die being a semiconductor substrate chip, and
wherein the first die is arranged on a surface of the substrate body of the second sensor such that the first die is arranged on top of the second die.

2. The sensor device according to claim 1,
wherein the first sensor is a gas sensor, and
wherein the second sensor is an environmental sensor configured to measure a relative humidity of a gas surrounding the sensor device.

3. The sensor device according to claim 1, wherein the first sensor is configured to heated up within a time of less than 2 seconds to an operating temperature that is between 300° C. and 500° C., inclusive, when in a sensing mode.

4. The sensor device according to claim 1, wherein the heating element is configured to heat up the second sensor to a maximum set point that is above an ambient temperature of an environment of the sensor device.

5. The sensor device according to claim 1, wherein the heating element is configured to heat up the second sensor at a lower rate than the first sensor.

6. The sensor device according to claim 1, further comprising a temperature sensor configured to measure a momentary temperature of the second sensor.

7. The sensor device according to claim 1,
wherein the heating element is operatable in a duty cycle when operated in a regular mode of operation, and
wherein, within an active time of the duty cycle, the first sensor is operatable in a sensing mode and the second sensor is operatable in an idle mode and vice versa, within a passive time of the duty cycle.

8. A method for operating a sensor device comprising a first die and a second sensor, wherein the first die comprises a first sensor with a heating element, wherein the second sensor is thermally coupled to the heating element of the first sensor, wherein the second sensor comprises a substrate body, the substrate body being a second die that comprises an integrated circuit, and wherein the first die is arranged on a surface of the substrate body of the second sensor so that the first die is arranged on top of the second die, the method comprising:
controllably heating up the second sensor to a set point using the heating element of the first sensor.

9. The method according to claim 8, further comprising
heating up, in a calibration mode, the second sensor to a number of calibration set points;
recording, at each of the number of calibration set points, a temperature-dependent measurement value with the second sensor; and
recording each measurement value with a corresponding one of the number of calibration set points in a calibration table and/or determining from the measurement values and calibration set points calibration coefficients.

10. The method according to claim 8, further comprising:
recording, in a self-diagnosis mode, a first measurement value of a temperature-dependent quantity when the second sensor is at a first test set point;
recording, in the self-diagnosis mode, a second measurement value of the temperature-dependent quantity when the second sensor is at a second test set point;
comparing the first measurement value to the second measurement value via a conserved quantity; and
based on a result of a comparison determining whether an error condition of the second sensor exists.

11. The method according to claim 8, further comprising:
detecting, in an aging-prevention mode, whether the second sensor is in a regime outside its specification; and
based on a result of a detection, heating the second sensor to a temperature set point that is higher than an ambient temperature of the sensor device.

12. The method according to claim 11, further comprising
recording, in the aging-prevention mode, an uncorrected measurement value at the temperature set point; and
calculating from the uncorrected measurement value and the temperature set point a corrected measurement value at the ambient temperature.

13. The method according to claim 8, further comprising:
heating, in a reconditioning mode, the second sensor to a reconditioning set point that depends on a boiling point of a contaminating compound; and
maintaining the second sensor at the reconditioning set point for an extended period such that the contaminating compound evaporates from the second sensor.

* * * * *